United States Patent [19]

Waterson

[11] Patent Number: 5,254,697

[45] Date of Patent: Oct. 19, 1993

[54] PROCESS FOR THE PREPARATION OF HALOALKYLLACTONES

[75] Inventor: David Waterson, Macclesfield, Great Britain

[73] Assignee: Imperial Chemical Industries PLC, London, England

[21] Appl. No.: 532,620

[22] Filed: Jun. 4, 1990

[30] Foreign Application Priority Data

Jun. 2, 1989 [GB] United Kingdom ............... 8912659

[51] Int. Cl.[5] .......................................... C07D 307/33
[52] U.S. Cl. ................................. 549/313; 549/321; 549/323; 549/324; 549/326
[58] Field of Search ............... 549/313, 321, 323, 324, 549/326; 548/230

[56] References Cited

U.S. PATENT DOCUMENTS 4,880,781 11/1989 Hester, Jr. et al. ................. 548/344

OTHER PUBLICATIONS

Evans, D. A., Aldrichimica Acta, vol. 15, No. 2, 1982, pp. 23-31.
Herold et al. II, J. Org. Chem. vol. 54, No. 5, Mar. 3, 1989 pp. 1178-1185.
Baker et al., Journal fo the Chemical Society, Perkin Transactions I, No. 1, Jan. 1988; pp. 85-97, Royal Society of Chemistry, "Enantiospecific synthesis of the spiroacetal moieties of avermectins A1b, B1b, A1a, B1a, A2b, B2b, A2a, and B2a and milbemcins alpha7 and alpha8", p. 96, compound 44.

Primary Examiner—C. Warren Ivy
Assistant Examiner—Ba K. Trinh
Attorney, Agent, or Firm—Cushman, Darby & Cushman

[57] ABSTRACT

The invention provides a novel process for the manufacture of enantiomerically-pure halolactones of the formula I which are useful for the production of certain 5-amino-4-hydroxyvaleric acid derivatives, themselves valuable intermediates in the production of compounds which are renin inhibitors. The process involves a diastereoselective alkylation of an oxazolidinone of the formula III, followed by a highly stereoselective and novel halolactonisation of an oxazolidinone of the formula II. Certain of the oxazolidinones of the formula II are novel and are provided as a further feature of the invention. The invention also provides a novel process for the production of the pharmaceutically-useful 5-amino-4-hydroxyvaleric acid derivatives of formula VI.

4 Claims, No Drawings

PROCESS FOR THE PREPARATION OF HALOALKYLLACTONES

This invention concerns a novel chemical process and, more particularly, it concerns a novel process for the manufacture of certain halolactones which are useful, for example, as chemical intermediates in the production of certain 5-amino-4-hydroxyvaleric acid derivatives. The invention is also concerned with certain novel oxazolidinones which are valuable chemical intermediates in the abovementioned process. The invention further concerns a novel process for the manufacture of said 5-amino-4-hydroxyvaleric acid derivatives.

In European Patent Application, Publication no. 258183 and J.Org.Chem., 1989, 54, 1178-1185 there is described the preparation of certain 5-amino-4-hydroxyvaleric acid derivatives useful as intermediates for the production of compounds which are inhibitors of the catalytic actin of renin, which compounds have been sought for use in the general control of hypertension and congestive heart failure, as well as for use in the diagnosis of hypertension due to excessive renin levels. In both of the above publications, the key intermediates for the production of said 5-amino-4-hydroxyvaleric acid derivatives are halolactones generated by halolactonisation of enantiomerically-pure gamma, delta-unsaturated carboxylic acids (or preferably their corresponding amide or hydroxamic ester derivatives) which are subsequently converted by a three-step reaction sequence into said 5-amino-4-hydroxyvaleric acid derivatives. The starting enantiomerically-pure gamma, delta-unsaturated carboxylic acids themselves are obtained using multi-step reaction sequences.

We have now discovered a convenient and useful alternative procedure for the production of said halolactones which does not necessitate the use of gamma, delta-unsaturated carboxylic acids, and which significantly reduces the number of synthetic steps required.

According to the invention there is provided a process for the manufacture of a halolactone of formula I (set out hereinafter), wherein $R^1$ is (3-8C)cycloalkyl, branched(3-6C)alkyl or phenyl, the latter group being unsubstituted or optionally bearing 1 or 2 substituents independently selected from halogeno, trifluoromethyl, cyano, (1-4C)alkyl and (1-4C)alkoxy; $R^2$ is a (1-6C)alkyl, (1-4C)alkoxy or (1-4C)alkylthio group; and X is a halogeno group; which comprises the steps of:

(i) reacting an oxazolidinone of the formula III (set out hereinafter), wherein $R^2$ has any of the meanings defined hereinbefore and $R^3$ is (1-6C)alkyl or phenyl(1-4C)alkyl the benzene ring of which may optionally bear 1 or 2 substituents independently selected from halogeno, (1-4C)alkyl and (1-4C)alkoxy, with a (2E)-butenyl halide of the formula IV (set out hereinafter) wherein Y is halogeno, and $R^1$ has any of the meanings defined hereinbefore, in the presence of a strong base, to give an oxazolidinone of the formula II (set out hereinafter) wherein $R^1$, $R^2$ and $R^3$ have any of the meanimgs defined above; and (ii) reacting the oxazolidinone of the formula II with a halogenating agent.

A particular value for $R^1$ when it is (3-8C)cycloalkyl is, for example, cyclopropyl, cyclobutyl, cyclopentyl or cyclohexyl; and when it is branched (3-6C)alkyl is, for example, isopropyl, isobutyl, sec-butyl, t-butyl or isopentyl.

Particular values for $R^2$ include the following, by way of example:

for (1-6C)alkyl: (1-4C)alkyl, such as methyl, ethyl, isopropyl or isobutyl;
for (1-4C)alkoxy: methoxy, ethoxy or propoxy; and
for (1-4C)alkylthio: methylthio or ethylthio.

A particular value for $R^3$ when it is (1-6C)alkyl is, for example, methyl, ethyl, isopropyl, isobutyl or sec-butyl; and when it is phenyl(1-4C)alkyl is, for example, benzyl, 1-phenylethyl or 2-phenylethyl.

A particular value for X is, for example, chloro, bromo or iodo, of which bromo is preferred.

Particular values for an optional substituent on $R^1$ when it is phenyl or on the benzene ring of $R^3$ when it is phenyl(1-4C)alkyl include, for example, fluoro, chloro, bromo, methyl, ethyl, methoxy and ethoxy.

A preferred value for $R^1$ is, for example, cyclohexyl.
A preferred value for $R^2$ is, for example, isopropyl.
A preferred value for $R^3$ is, for example, benzyl.

The reaction step (i) is generally carried out in a suitable solvent or diluent, for example, an ether such as t-butyl methyl ether, diethyl ether or tetrahydrofuran, or a hydrocarbon such as hexane, or in a mixture of one or more such solvents or diluents. Reaction step (i) is generally performed at a temperature in the range, for example, $-60°$ C. to $30°$ C.

A particularly suitable strong base for use in reaction step (i) is, for example, an alkali metal alkane such as butyllithium, or an alkali metal salt of a secondary amine such as lithium diisopropylamide.

A particularly suitable value for Y in a compound of the formula IV is, for example, chloro, bromo or iodo, of which bromo and iodo are preferred.

The starting (2E)-butenyl halides of the formula IV may be obtained by reacting a compound of the formula $R^1CH_2.CH(OH).CH=CH_2$ (formula V) with a suitable halogenating agent, for example, thionyl chloride or bromide. The reaction may be carried out in the absence of any solvent or in the presence of an inert solvent or diluent, for example, a hydrocarbon such as toluene or hexane, or an ether such as t-butyl methyl ether or diethyl ether, and at a temperature in the general range of $0°$ C. to $100°$ C., and preferably at or near ambient temperature.

Alternatively, a compound of the formula IV wherein Y is iodo may be obtained by reacting a compound of the formula IV wherein X is chloro or bromo with an alkali metal iodide (such as sodium iodide), generally in the presence of a suitable inert solvent or diluent (such as acetone), at a temperature in the general range of $0°$ C. to $100°$ C., and preferably at or near ambient temperature.

The starting oxazolidinones of the formula III are known or can be made by conventional procedures of organic chemistry.

The reaction step (ii) is generally carried out in the presence of a suitable solvent or diluent or a combination thereof, for example, in a generally aqueous environment, using water or a mixture of water and an inert organic solvent selected from, for example, a lover alcohol (such as methanol), an ether (such as 1,2-dimethoxyethane, tetrahydrofuran or dioxane) or a halohydrocarbon (such as dichloromethane or chloroform), and optionally in the presence of acetic acid. Additionally, step (ii) may be conveniently carried out at a temperature in the general range, for example, $-30°$ C. to $80°$ C., and preferably between $0°$ C. and $30°$ C.

A particularly suitable halogenating agent for use in reaction step (ii) is, for example, iodine, bromine or other positive halogen releasing agent such as N- iodosuccinimide, N-bromosuccinimide or N-chlorosuccinimide, of which N-bromosuccinimide is preferred.

It will be seen that the process of the invention is significantly shorter than the procedures described in the prior art which latter involve the use of gamma, delta-unsaturated carboxylic acids. The present invention involves a diastereoselective alkylation of a compound of the formula III followed by a highly stereoselective and novel halolactonisation of a compound of formula II to generate an enantiomerically-pure halolactone of formula I. This avoids the need for conversion of a formula II compound to a gamma, delta-unsaturated carboxylic acid, followed by amide formation, prior to halolactonisation.

A number of the oxazolidinones of formula II are novel, for example, those wherein $R^3$ is phenyl(1-4C)alkyl bearing 1 or 2 optional substituents as defined hereinbefore, and are provided as a further feature of the invention.

The invention further provides an improved process for the production of a pharmaceutically-useful 5-amino-4-hydroxyvaleric acid derivative of the formula VI (set out hereinafter) wherein $R^1$ and $R^2$ have any of the values defined above and $R^4$ and $R^5$ are independently selected from hydrogen and an optional substituent which comprises:

(i) reacting an oxazolidinone of the formula III (set out hereinafter) wherein $R^2$ and $R^3$ have any of the meanings defined hereinbefore, with a (2E)-butenyl halide of the formula IV (set out hereinafter) wherein Y is halogeno and $R^1$ has any of the meanings defined hereinbefore, in the presence of a strong base, to give an oxazolidinone of the formula II (set out hereinafter) wherein $R^1$, $R^2$ and $R^3$ have any of the meanings defined above; followed by (ii) reacting an oxazolidinone of the formula II with a halogenating agent to give a halo-1-actone of the formula I (set out hereinafter) wherein $R^1$, $R^2$ and X have any of the meanings defined above; followed by (iii) reacting a halolactone of the formula I with an alkali metal azide to give an azide of the formula VII (set out hereinafter) wherein $R^1$ and $R^2$ have any of the meanings defined above; followed by (iv) reacting an azide of the formula VII with an amine of the formula $R^4R^5NH$ to give a compound of the formula VIII (set out hereinafter) wherein $R^1$, $R^2$, $R^4$ and $R^5$ have any of the meanings defined above; followed by (v) reducing a compound of the formula VIII to give said 5-amino-4-hydroxyvaleric acid derivative of formula VI; whereafter, when a non-toxic salt is required said compound of formula VI is reacted with the appropriate acid having a non-toxic anion.

Reaction steps (iii), (iv) and (v) can be carried out using analogous procedures to those described in the prior art.

Alternatively, steps (iv) and (v) may be replaced by the following procedure:

(a) reducing a compound of the formula VII to give a compound of the formula IX (set out hereinafter) wherein $R^1$ and $R^2$ have any of the meanings defined above; followed by (b) reacting a compound of the formula IX with an amine of the formula $R^4R^5NH$ to give said 5-amino-4-hydroxyvaleric acid derivative of formula VI.

In certain cases it may be necessary, prior to carrying out step (b) to protect the amino substituent of a compound of the formula IX and then remove the protecting group as a final step.

However, it will be appreciated that the above process may be used to produce any of the known pharmaceutically-useful 5-amino-4-hydroxyvaleramides described in European Patent Application, Publication No. 258183, or in our co-pending British Patent Application No. 8826930.3, by use of the appropriate amine of the formula $R^4R^5NH$, for example, butylamine, 2-dimethylaminoethylamine, N-methylbutylamine, 2-aminoethylamine, 3-aminopropylamine, 3-aminomethylpyridine, 2-(N-morpholino)ethylamine or morpholine.

The invention will now be illustrated by the following non-limiting Examples in which, unless otherwise stated:

(i) all evaporations were carried out by rotary evaporation in vacuo;

(ii) all operations were carried out at room temperature, that is in the general range 18°-26° C.;

(iii) purification by flash chromatography was performed on silica (Merck Kieselgel: Art 9385) using the procedure described in J. Org. Chem., 1978, 43, 2923, following the purification by thin layer chromatography on silica (0.25 mm, Merck Kieselgel 60F 254 plates: art.5715; materials available from E Merck, Darmstadt, Federal republic of Germany;

(iv) the purity and chemical composition of products was assessed by nuclear magnetic resonance (NMR) spectroscopy, thin layer chromatographic analysis, mass spectroscopy and/or microanalysis;

(v) NMR spectra were determined at 200 MHz in $CDCl_3$ using tetramethyl silane (TMS) as an integral standard and are given as chemical shifts in parts per million relative to TMS, using conventional abbreviations for signals, such as: s, singlet; d, doublet; dd, doublet of doublets; t, triplet; m, multiplet; br, broad; and (vi) yields are given for illustration purposes only and are not necessarily the maximum attainable following diligent process development.

EXAMPLE 1

N-Bromosuccinimide (13.7 g) was added to a stirred mixture of (4S)-4-benzyl-3-[(2S,4E)-6-cyclohexyl-2-isopropylhex-4-enoyl]oxazolidin-2-one (A) (27.9 g) in dimethoxyethane (75 ml) and water (75 ml) at 0° C. The mixture was stirred at 0° C. for 10 minutes and then at ambient temperature overnight. Water (500 ml) was added and the mixture was extracted with ether (3×250 ml). The extracts were washed with saturated sodium hydrogen carbonate solution (250 ml), followed by saturated sodium chloride solution (250 ml) and then dried ($MgSO_4$). The solvent was removed by evaporation and the residue was purified by flash chromatography, eluting with ethyl acetate/hexane (1:9 v/v, gradually increasing to 3:17 v/v) to give (3S,5S)-5-[(1R)-(1-bromo-2-cyclohexyl)ethyl]-3-isopropyltetrahydrofuran-2-one as a white solid, m.p. 95° C. (after two recrystallisations from hexane); in 30% yield; NMR: 0.7-1.4(complex m, 12H), 1.7(complex m, 6H), 2.2(complex m, 3H), 2.7(ddd, 1H), 4.15(ddd, 1H), 4.4(dt, 1H); infrared spectrum: 1775 cm$^{-1}$ (lactone carbonyl); mass spectrum (positive chemical ionisation) 334 (M+NH$_4$)$^+$, 317 (M+H)$^+$, 237, 127; $^{22}[\alpha]_D$+31.9°(c, 1.0, $CHCl_3$); microanalysis, found: C, 56.5; H, 7.9; Br, 25.2%; $C_{15}H_{25}BrO_2$ requires: C, 56.8; H, 7.9; Br, 25.2%.

The starting material (A) was obtained as follows:

(i) Thionyl chloride (50.5 ml) was added dropwise over 1 hour to a stirred solution of 1-cyclohexyl-3-buten-2-ol (50 g) (obtained as described in European Patent Application, Publication No. 258183) in dry ether (1 litre). The solution was allowed to stand overnight and then water (750 ml) was added, and the mixture was stirred for 1 hour. The organic phase was separated, washed with water (500 ml) and saturated sodium chloride solution (2×250 ml) and dried (MgSO₄). The solvent was removed by evaporation and the residual liquid distilled under high vacuum to give (2E)-1-chloro-4-cyclohexylbut-2 -ene (B), as a clear liquid (42.2 g), b.p. 64-68° C. at 0.5 mm Hg; NMR: 0.8-1.8(complex m, 11H), 2.0(t, 2H), 4.0(d, 2H), 5.5-5.9(complex m, 2H); microanalysis, found: C, 69.5; H, 10.0; Cl, 20.3%; C₁₀H₁₇Cl requires: C, 69.5; H, 9.9; Cl, 20.5%.

(ii) The chloride (B) (38.6 g) was added to a solution of sodium iodide (55.7 g) in acetone (1 litre) and the solution was allowed to stand overnight. Hexane (500 ml) was added and the precipitated solid was removed by filtration. The filtrate was concentrated and the residue partitioned between water (500 ml) and hexane (500 ml). The organic phase was separated, washed with saturated sodium thiosulphate solution (500 ml) and saturated sodium chloride solution (2×500 ml), and dried (MgSO₄). The solvent was removed by evaporation and the residual liquid distilled under vacuum to give (2E)-4-cyclohexyl-1-iodobut-2-ene (C) as a dark liquid (44.9 g), b.p. 80°-85° C. at 0.15 mm Hg; NMR: 0.8-1.8(complex m, 11H), 1.9(t, 2H), 3.9(m, 2H), 5.7(m, 2H). (iii) A 1.6M solution of butyllithium in hexane (93.9 ml) was added dropwise over 30 minutes to a stirred solution of diisopropylamine (21.9 ml) in dry tetrahydrofuran (THF) (200 ml) at 0° C. under an atmosphere of argon. The temperature was maintained at 0° C. for 30 minutes and then the solution was cooled to −40° C. A solution of (4S)-4-benzyl-3-(3-methyl-butyryl)oxazolidin-2-one (31.3 g) (obtained as described in *Tetrahedron*. 1987, 44, 5525) in dry THF (70 ml) was added dropwise over 30 minutes. The solution was kept at −40° C. for 30 minutes and then the temperature was allowed to rise to 0° C. A solution of iodide (C) (39.0 g) in dry THF (75 ml) was added dropwise over 30 minutes, and then the solution was stirred at 0° C. for 1 hour. Saturated sodium chloride solution (250 ml) was added and the mixture was extracted with ether (3×250 ml). The extracts were washed with saturated sodium chloride solution (2×250 ml) and dried (MgSO₄). The solvent was removed by evaporation and the residue was purified by flash chromatography, eluting with ethyl acetate/hexane (8:92 v/v), to give (4s)-4-benzyl-3-[(2S,4E)-6-cyclohexyl-2-isopropylhex-4-enoyl]oxazolidin-2-one (A) (34.5 g) as a clear oil; NMR: 0.8 -1.2(complex m, 12H), 1.6(m, 6H), 1.85(t, 1H), 2.0(m, 2H), 2.35(m, 2H), 2.6(m, 1H), 3.3(dt, 1H), 3.8(m, 1H), 4.1(d, 1H), 4.7(m, 1H), 5.4(m, 2H), 7.3(m, 5H); mass spectrum (+ve FAB), 398 (M+H⁺); $^{22}[\alpha]_{436}$+45.8 (c, 1.04, CHCl₃).

CHEMICAL FORMULAE

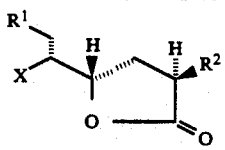

I

-continued

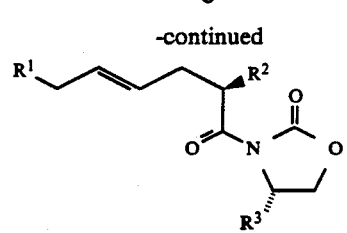

II

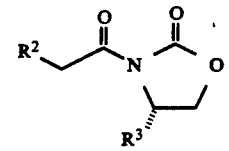

III

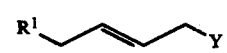

IV

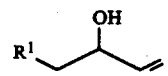

V

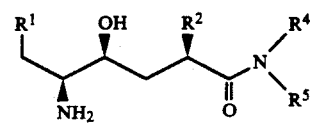

VI

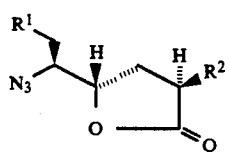

VII

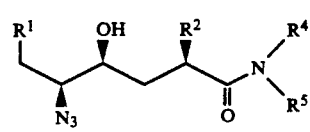

VIII

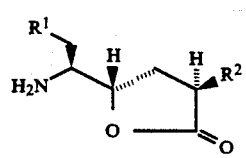

IX

What we claim is:

1. A process for the manufacture of a halolactone of the formula I

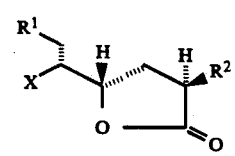

I wherein R¹ is (3-8C)cycloalkyl, branched(3-6C)alkyl or phenyl, the latter group being unsubstituted or optionally bearing 1 or 2 substituents independently selected from halogeno, trifluoromethyl, cyano, (1-4C)alkyl and (1-4C)alkoxy; R² is a (1-6C)alkyl, (1-4C)alkoxy or (1-4C)alkylthio group; and X is a halogeno group; characterised by:

(i) reacting an oxazolidinone of the formula III

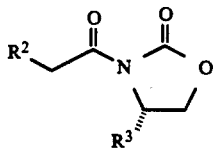

wherein $R^2$ has any of the meanings defined above and $R^3$ is (1-6C)alkyl or phenyl(1-4C)alkyl the benzene ring of which may optionally bear 1 or 2 substituents independently selected from halogeno, (1-4C)alkyl and (1-4C)alkoxy, with a (2E)-butenyl halide of the formula IV

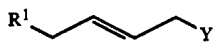

wherein Y is halogeno and $R^1$ has any of the meanings defined above, in the presence of a strong base, to give an oxazolidinone of the formula

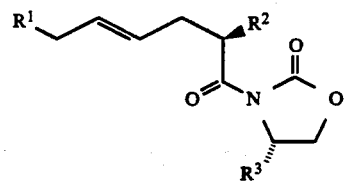

wherein $R^1$, $R^2$ and $R^3$ have any of the meanings defined above; followed by (ii) reacting the oxazolidinone of the formula II with a halogenating agent.

2. A process as claimed in claim 1 characterised in that in the starting materials $R^1$ is cyclopropyl, cyclobutyl, cyclopentyl, cyclohexyl, isopropyl, isobutyl, sec-butyl, t-butyl, isopentyl or phenyl, the latter group being unsubstituted or optionally bearing 1 or 2 substituents independently selected from fluoro, chloro, bromo, trifluoromethyl, cyano, methyl, ethyl, methoxy and ethoxy; $R^2$ is a (1-4C)alkyl, methoxy, ethoxy, propoxy, methylthio or ethylthio group; and $R^3$ is methyl, ethyl, isopropyl, isobutyl, sec-butyl, benzyl, 1-phenylethyl or 2-phenylethyl, the benzene ring of which last three groups may optionally bear 1 or 2 substituents independently selected from fluoro, chloro, bromo, methyl, ethyl, methoxy and ethoxy.

3. A process as claimed in claim 1 or 2 characterised in that in the starting materials $R^1$ is (3-8C)cycloalkyl; $R^2$ is (1-4C)alkyl; and $R^3$ is phenyl(1-4C)alkyl, the benzene ring of which may optionally bear 1 or 2 substituents independently selected from halogeno, (1-4C)alkyl and (1-4C)alkoxy.

4. A process as claimed in claims 1, 2 or 3 characterised in that in the starting materials the halogenating agent is selected from N-chlorosuccinimide, N-bromosuccinimide and N-iodosuccinimide.

* * * * *